(12) United States Patent
Navab et al.

(10) Patent No.: US 6,236,704 B1
(45) Date of Patent: May 22, 2001

(54) METHOD AND APPARATUS USING A VIRTUAL DETECTOR FOR THREE-DIMENSIONAL RECONSTRUCTION FROM X-RAY IMAGES

(75) Inventors: Nassir Navab, E. Windsor, NJ (US); Matthias Mitschke, Nuremberg (DE)

(73) Assignee: Siemens Corporate Research, Inc., Princeton, NJ (US)

( * ) Notice: Subject to any disclaimer, the term of this patent is extended or adjusted under 35 U.S.C. 154(b) by 0 days.

(21) Appl. No.: 09/345,076

(22) Filed: Jun. 30, 1999

(51) Int. Cl.[7] .................................................... A61B 6/03
(52) U.S. Cl. ................................. 378/4; 378/19; 378/901
(58) Field of Search .................................. 378/4, 15, 19, 378/901

(56) References Cited

U.S. PATENT DOCUMENTS 5,559,335 * 9/1996 Zeng et al. ...................... 250/363.04

* cited by examiner

Primary Examiner—David V. Bruce

(57) ABSTRACT

Compensation can be provided for rotational and translational motion of a detector relative to the X-ray source in a C-arm X-ray device by warping the image on the detector plane to a virtual detector plane and then mapping the image into three-dimensional space. By using a virtual detector, the computations required to reconstruct the three-dimensional model are greatly simplified.

12 Claims, 4 Drawing Sheets

METHOD AND APPARATUS USING A VIRTUAL DETECTOR FOR THREE-DIMENSIONAL RECONSTRUCTION FROM X-RAY IMAGES

BACKGROUND OF THE INVENTION

In a C-arm X-ray system, as shown schematically in FIG. 1, an X-ray source 10 projects energy through an object of interest 20, rotating about the object and creating a series of two-dimensional images on a detector 30. To reconstruct a three-dimensional model of an object 20 as detected by the X-ray source 10, the images are "back projected" (i.e., projected back) from the detector 30 into the three-dimensional space divided into voxels where the object 20 was located, at corresponding angles of rotation. In an idealized system, the detector 30 is fixed in space relative to the source 10 and therefore the only factors of interest are the angle of rotation and possible translational motion of the X-ray source 10.

In a practical implementation of the C-arm, the arm flexes as it rotates, is changing the relative position and orientation between the source and detector, as well as their position and orientation in space relative to the object of interest. To accurately reconstruct the images into a useful virtual three-dimensional model, compensation for such motion is required.

DESCRIPTION OF THE INVENTION

By warping the image on the physical detector onto a virtual detector plane fixed in space with respect to the X-ray source, the image can then be mapped into three-dimensional voxels without having to account for rotation and translation of the detector with respect to the X-ray source.

Figure 2:
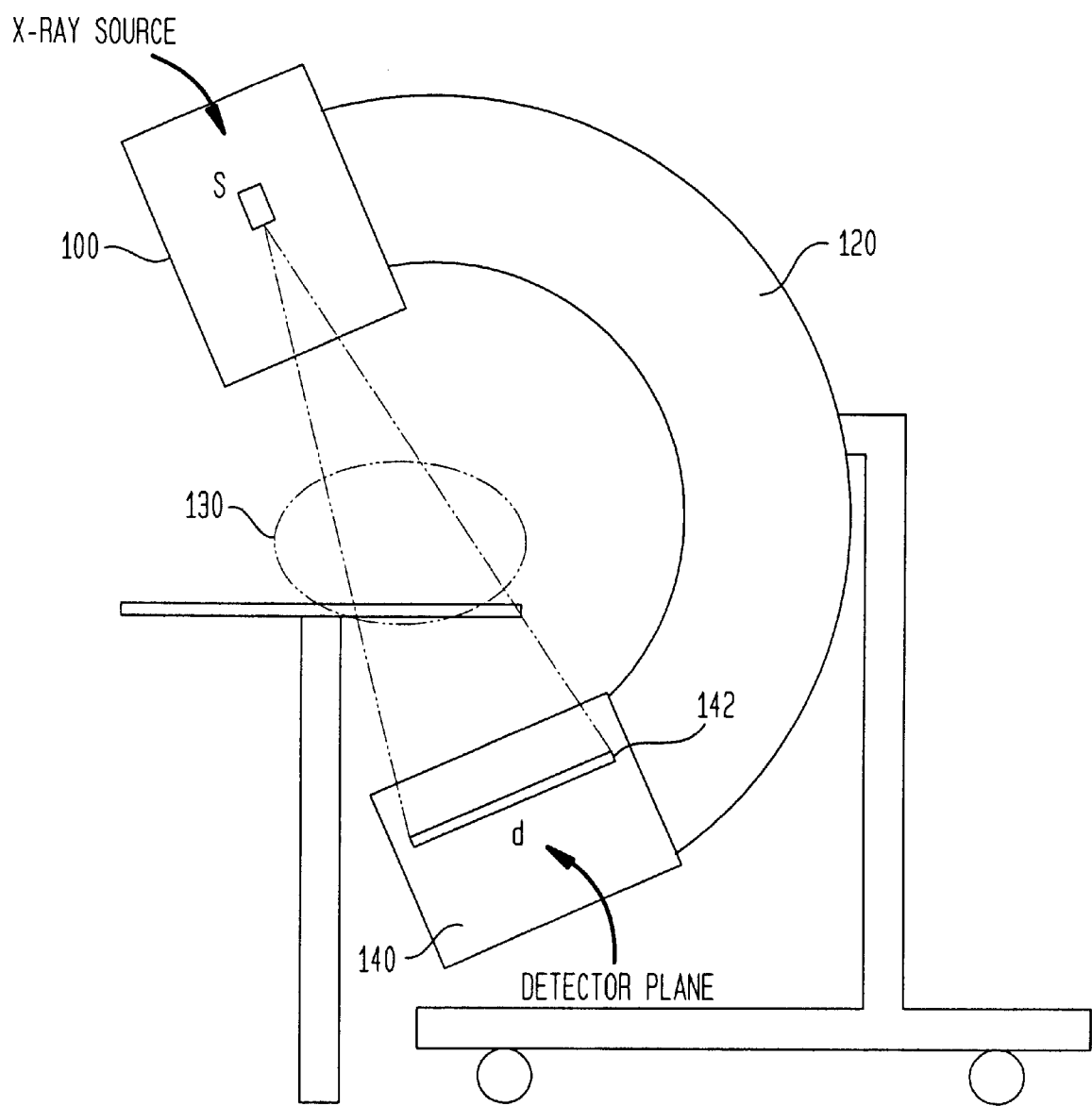
FIG. 2 is a diagram of a C-arm X-ray system.
Figure 4:
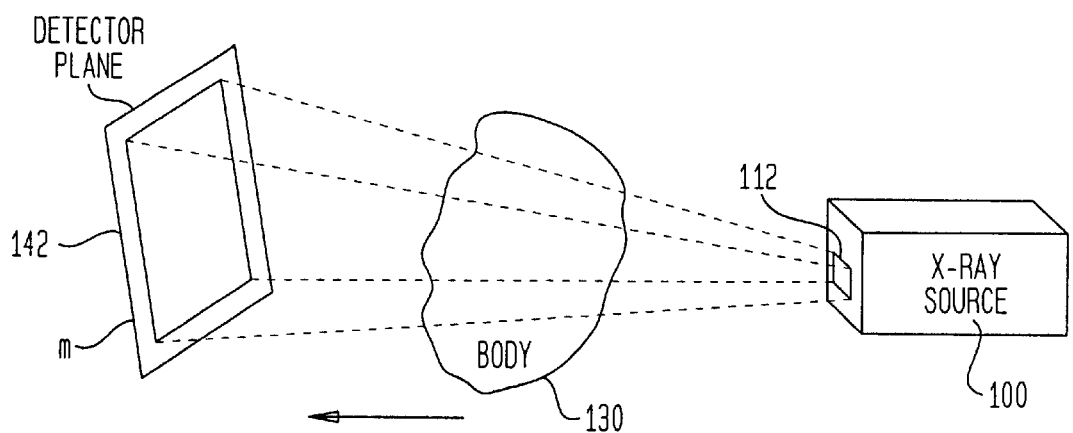
FIGS. 4–6 illustrate the processes of image generation, warping, and back-projection, respectively.

In FIG. 2, a mobile C-arm X-ray system has a source 100 mounted on a C-arm 120 that projects energy through an object 130 towards a detector 140, forming an image on a detector plane 142. In this first step, shown in FIG. 4, the three-dimensional (3D) object 130 has been projected onto the detector plane 142 to create a two-dimensional (2D) image. As noted, although the C-arm 120 is ideally a rigid structure, it does flex slightly as it rotates about the object, changing the distance between the source 100 and the detector plane 142 as well as the spatial relationship between the two. To accurately reconstruct the object 130 based on a series of X-ray images generated as the C-arm 120 rotates about the object, one must compensate for the relative motion of the X-ray source 100 with respect to the detector plane 142.

Figure 1:
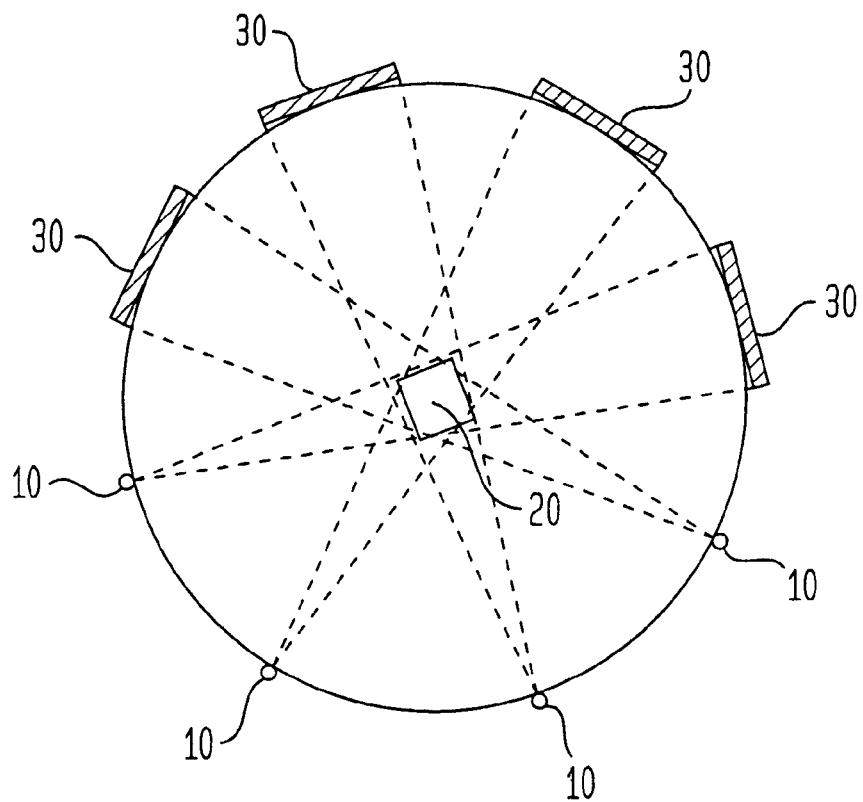
FIG. 1 is a conceptual diagram of the operation of an ideal C-arm X-ray system.
Figure 3:
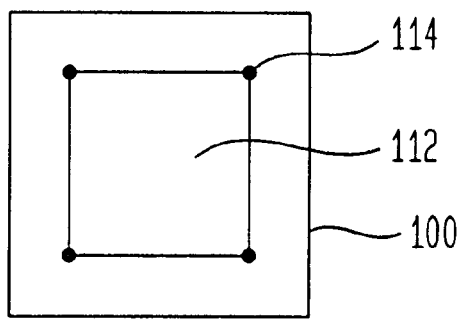
FIG. 3 is a diagram of an X-ray source with a marker plate.

As discussed in commonly-assigned, co-pending U.S. patent application Ser. No. 09/211,347, filed on Dec. 15, 1998, incorporated by reference herein, and shown in FIG. 3, a marker plate 112 of individual markers 114, of some geometry and pattern (e.g., square, rectangular, etc.) is positioned on the source 100. When X-ray energy issues from the source 100, it passes through the marker plate 112 and the image of the markers 114 is projected onto the detector 140, providing an indication of the spatial relationship and orientation between the object 130 and the image on the detector plane 142.

Since the spatial relationship between the source 100 and the detector plane 142 varies as the C-arm 120 rotates, the aspect of the marker plate 112 on the detector plane 142 will vary and thus a reconstruction of the two-dimensional image into a three-dimensional virtual object will arguably require a different set of calculations for each image. However, by warping the two-dimensional image onto a virtual image plane 150 fixed in space relative to the source 100, the subsequent transformation (or back projection) from the virtual image plane 150 into three-dimensional space divided into voxels 160 is simplified.

The location of the virtual detector 150 can be defined by the user as an arbitrary location in space. For example, the location of the actual detector plane 142 when the first image is created may be selected as the location of the virtual detector 150. In that instance, no warping would be required to the virtual plane 150, as they would be identical. Subsequent images would then be warped to this location in space, with relatively minimal warping.

Figure 5:
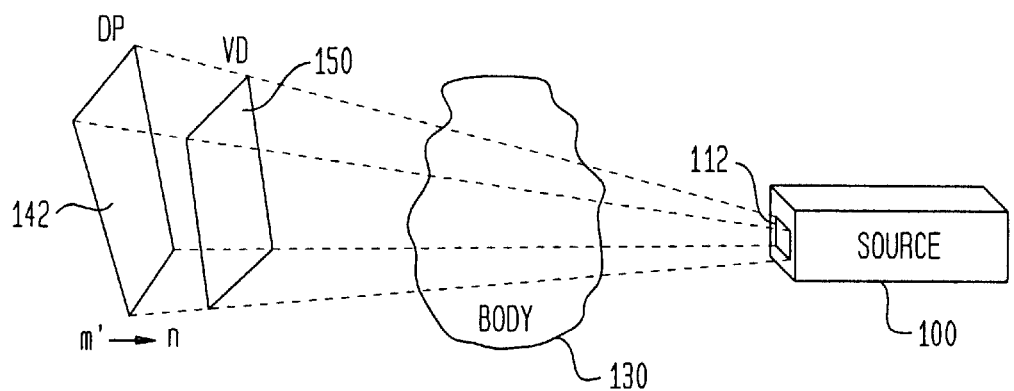
Figure 7:
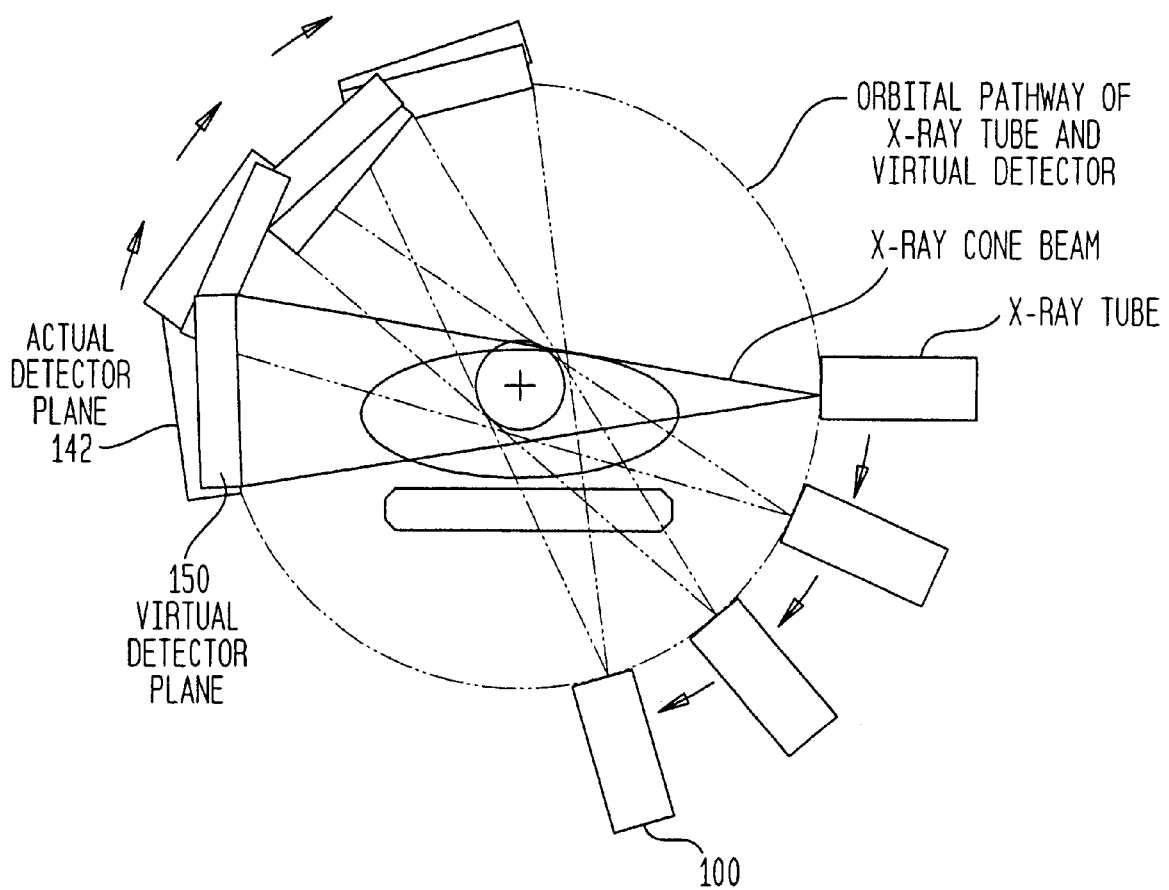
FIG. 7 is a drawing showing the rotation of the X-ray source around the object, and the actual and virtual detector planes.

Warping of the image from the detector plane 142 is accomplished by applying a planar transformation matrix H to the image of the marker plate 112 until it conforms to the aspect and dimensions the marker plate would assume had it been initially projected onto the virtual image plane 150 (FIGS. 5 and 7). For each pixel in the detector image, matrix H calculated for the particular location of the detector plane 142, is multiplied by the position of that pixel to produce the position of the corresponding pixel in the virtual image plane 150.

The matrix H is calculated by using techniques well known in the art. Such methods are described in, for example, U.S. Pat. No. 5,821,943 and U.S. Pat. No. 5,845,639, incorporated herein by reference, and in Wolberg, "Digital Image Warping," IEEE Computer Society Press, Los Alamitos, Calif. 1990.

Figure 6:
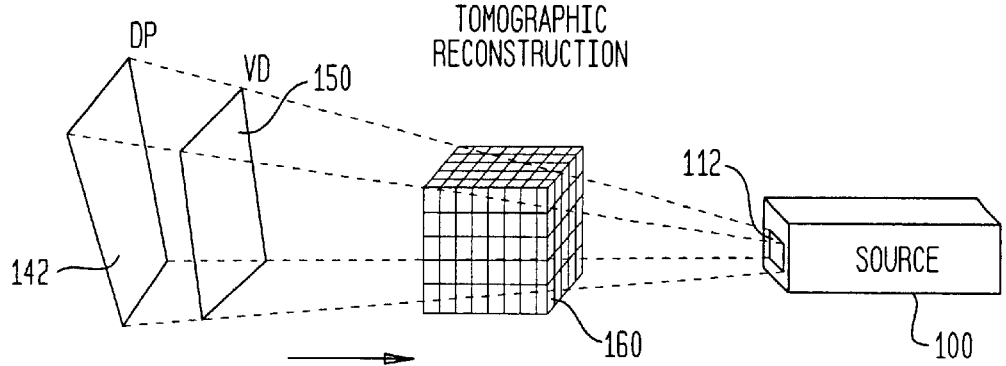

To reconstruct the object from images captured as the C-arm 120 rotates, the images are now back projected into the voxels 160 lying in the region of interest (FIG. 6). To do so, the system must (1) provide a method for mapping the two-dimensional images into the three-dimensional voxels and (2) account for motion of the C-arm 120 (and therefore the axis between the source 100 and the detector plane 142) relative to the object 130.

Methods for mapping two-dimensional images into three-dimensional voxels are described in, for example, U.S. Pat. No. 5,822,396 and U.S. Pat. No. 5,835,563, incorporated by reference herein. These methods will yield a "projection matrix" P, which is multiplied by the set of points in the image in the virtual detector plane 150 to map them to points in the three-dimensional voxels.

Compensation for motion of the C-arm 120 relative to the object 130 can be achieved using the method and apparatus described in commonly-assigned co-pending patent application Ser. No. 08/940,923, for a "Method and Apparatus for Calibrating an Intra-Operative X-Ray System," filed Sep. 30, 1997, incorporated herein by reference. This method will yield a matrix providing components of rotation and translation for effectively shifting the back-projected points to compensate for the motion of the C-arm 120.

The warping and mapping operations can be represented by the following equations:

$$m_i' = Hm_i$$

where: $m_i$ are the pixels in the actual detector plane;
H is the planar transformation matrix mapping pixels on the virtual detector to the actual detector plane; and
$m_i$ are the pixels in the virtual detector plane.

$$\tilde{P}_x' = HP_x \begin{bmatrix} R & T \\ 0^T & 1 \end{bmatrix}$$

where: $\tilde{P}_x'$ is the projection matrix mapping the three-dimensional voxels to the two-dimensional pixels on the actual detector plane;
$P_x$ is the original projection matrix mapping the three-dimensional voxels to the two-dimensional pixels on the virtual detector plane;
is the planar transformation matrix mapping pixels on the virtual detector to the actual detector plane;
R is the rotation matrix representing the rotational motion of the X-ray source; and
T is the translation vector representing the translational motion of the X-ray source.

The bases for these equations can be found in the references previously cited. It is understood that such calculations are typically performed by a computer.

While the present invention has been described by way of exemplary embodiments, it will by understood by one of skill in the art to which it pertains that various changes and modifications can be made.

For example, it is possible to use dedicated computer hardware such as "graphics accelerator hardware" for image warping or texture mapping. A number of commercially available computers are so equipped. For another example, virtual detector 150 is illustrated in the drawing as being located between detector plane 142 and source 100. It is contemplated in the present invention that the virtual detector may be located beyond or behind detector plane 142, or between the X-ray source 100 and 3-dimensional space 160. Furthermore, virtual detector 150, shown illustrated as being parallel to detector plane 142, may be set at an angle. It should be understood that these and the like changes can be made without departing from the spirit of the invention, which is defined by the claims following.

What is claimed is:

1. A method, comprising the steps of:
   directing a source of X-ray energy from a plurality of angles through an object of interest onto a detector plane, creating images on the detector plane;
   warping the images on the detector plane onto a virtual detector plane fixed in space with respect to the source; and
   back-projecting the images on the virtual detector into three-dimensional space.

2. A method as set forth in claim 1, where the step of warping the images on the detector plane onto a virtual detector plane comprises the step of applying a planar transformation to the images.

3. A method as set forth in claim 1, where the step of warping the images on the detector plane onto a virtual detector plane comprises the step of selecting the detector plane for one of the images as the virtual detector plane.

4. A method as set forth in claim 1, where
   the step of directing a source of X-ray energy through an object of interest comprises the step of directing the source from a marker plate; and
   the step of warping the image on the detector plane onto a virtual detector plane comprises the step of warping the image with respect to the aspect of the image of the marker plate on the detector plane.

5. An apparatus, comprising:
   means for directing a source of X-ray energy from a plurality of angles through an object of interest onto a detector plane, creating images on the detector plane;
   means for warping the images on the detector plane onto a virtual detector plane fixed in space with respect to the source; and
   means for back-projecting the images on the virtual detector into three-dimensional space.

6. An apparatus as set forth in claim 5, where the means for warping the images on the detector plane onto a virtual detector plane comprises means for applying a planar transformation to the images.

7. An apparatus as set forth in claim 5, where the means for warping the images on the detector plane onto a virtual detector plane comprises means for selecting the detector plane for one of the images as the virtual detector plane.

8. An apparatus as set forth in claim 5, where
   the means for directing a source of X-ray energy through an object of interest comprises means for directing the source from a marker plate; and
   the means for warping the image on the detector plane onto a virtual detector plane comprises means for warping the image with respect to the aspect of the image of the marker plate on the detector plane.

9. An apparatus, comprising:
   C-arm X-ray apparatus for directing a source of X-ray energy from a plurality of angles through an object of interest onto a detector plane, creating images on the detector plane;
   computer apparatus, including data storage apparatus, for warping the images on the detector plane onto a virtual detector plane fixed in space with respect to the source; and
   image-processing apparatus for back-projecting the images on the virtual detector into three-dimensional space.

10. An apparatus as set forth in claim 9, where the computer apparatus for warping the images on the detector plane onto a virtual detector plane comprises programmable computer apparatus for applying a planar transformation to the images.

11. An apparatus as set forth in claim 9, where the computer apparatus for warping the images on the detector plane onto a virtual detector plane comprises computer apparatus for selecting the detector plane for one of the images as the virtual detector plane.

12. An apparatus as set forth in claim 9, where
   the C-arm X-ray apparatus for directing a source of X-ray energy through an object of interest comprises apparatus for directing the source from a marker plate; and
   the computer apparatus for warping the image on the detector plane onto a virtual detector plane comprises computer means for warping the image with respect to the aspect of the image of the marker plate on the detector plane.

* * * * *